US011776154B2

United States Patent
König et al.

(10) Patent No.: US 11,776,154 B2
(45) Date of Patent: Oct. 3, 2023

(54) METHOD AND DEVICE FOR MEDICAL IMAGING FOR REPRESENTING A 3D VOLUME CONTAINING AT LEAST ONE INTRODUCED FOREIGN OBJECT

(71) Applicant: Ziehm Imaging GmbH, Nuremberg (DE)

(72) Inventors: Thomas König, Nuremberg (DE); Klaus Hörndler, Nuremberg (DE); Eva-Maria Ilg, Nuremberg (DE); Christof Fleischmann, Möhrendorf (DE); Lars Hillebrand, Weisendorf (DE)

(73) Assignee: Ziehm Imaging GmbH, Nuremberg (DE)

( * ) Notice: Subject to any disclaimer, the term of this patent is extended or adjusted under 35 U.S.C. 154(b) by 92 days.

(21) Appl. No.: 16/867,408

(22) Filed: May 5, 2020

(65) Prior Publication Data

US 2020/0402255 A1  Dec. 24, 2020

(30) Foreign Application Priority Data

Jun. 18, 2019  (DE) .................... 10 2019 004 303.0

(51) Int. Cl.
*G06T 7/73* (2017.01)
*A61B 6/03* (2006.01)
(Continued)

(52) U.S. Cl.
CPC ................ *G06T 7/73* (2017.01); *A61B 6/032* (2013.01); *A61B 6/4085* (2013.01);
(Continued)

(58) Field of Classification Search
CPC ......... A61B 6/032; A61B 6/12; A61B 6/4085; A61B 6/4441; A61B 6/466; G06T 7/11;
(Continued)

(56) References Cited

U.S. PATENT DOCUMENTS

2006/0072844 A1* 4/2006 Wang ...................... G06T 5/003
382/254
2006/0079743 A1* 4/2006 Ferrant .................... G06T 7/64
600/407

(Continued)

FOREIGN PATENT DOCUMENTS

DE  10 2013 204 552  9/2014

OTHER PUBLICATIONS

Bal et al. "A radial adaptive filter for metal artifact reduction." Medical Imaging 2005: Image Processing. vol. 5747. International Society for Optics and Photonics, 2005. (Year: 2005).*

(Continued)

*Primary Examiner* — Katrina R Fujita
(74) *Attorney, Agent, or Firm* — Knobbe, Martens, Olson & Bear LLP

(57) ABSTRACT

Medical imaging systems and methods for representing a 3D volume containing at least one foreign object introduced into a tissue. Imaging methods may include provision of a 3D volume containing voxels of at least one foreign object and voxels of tissue surrounding the at least one foreign object, identification of the voxels of the at least one foreign object by application of a processing rule, segmentation of the voxels of the at least one foreign object from the voxels of the tissue surrounding the at least one foreign object while maintaining the 3D volume, generation of a synthetic volume from a residual volume and the volume of the at least one foreign object, and representation of the synthetic volume on a display device using a windowing system.

16 Claims, 3 Drawing Sheets

(51) Int. Cl.
　　　A61B 6/00　　　　(2006.01)
　　　G06T 7/11　　　　(2017.01)
　　　G06T 7/60　　　　(2017.01)
　　　G06T 7/174　　　(2017.01)
(52) U.S. Cl.
　　　CPC .............. *A61B 6/4441* (2013.01); *G06T 7/11* (2017.01); *G06T 7/174* (2017.01); *G06T 7/60* (2013.01); *G06T 2207/10028* (2013.01); *G06T 2207/10081* (2013.01); *G06T 2207/20081* (2013.01); *G06T 2207/30052* (2013.01); *G06T 2207/30204* (2013.01)
(58) Field of Classification Search
　　　CPC .. G06T 7/174; G06T 7/60; G06T 7/73; G06T 19/00; G06T 2207/10028; G06T 2207/10072; G06T 2207/10081; G06T 2207/10116; G06T 2207/20081; G06T 2207/30012; G06T 2207/30052; G06T 2207/30204; G06T 2210/41
　　　See application file for complete search history.

(56) References Cited

U.S. PATENT DOCUMENTS

| | | | |
|---|---|---|---|
| 2008/0089566 A1* | 4/2008 | Node-Langlois | G06T 7/30 382/128 |
| 2011/0052018 A1* | 3/2011 | Blaffert | G06T 7/149 382/128 |
| 2014/0010431 A1 | 1/2014 | Stayman et al. | |
| 2014/0267255 A1* | 9/2014 | Graumann | G06T 19/00 345/420 |
| 2015/0078647 A1 | 3/2015 | Helm et al. | |
| 2016/0307330 A1* | 10/2016 | Goshen | G06T 7/11 |
| 2019/0147639 A1* | 5/2019 | Sudarsky | A61B 5/1073 345/424 |
| 2020/0297425 A1* | 9/2020 | Helm | A61B 34/25 |

OTHER PUBLICATIONS

Stayman et al. "Model-based tomographic reconstruction of objects containing known components." IEEE transactions on medical imaging 31.10 (2012): 1837-1848. (Year: 2012).*

Examination Report, Application No. 10 2019 004 303.0, dated Jan. 22, 2020.

* cited by examiner

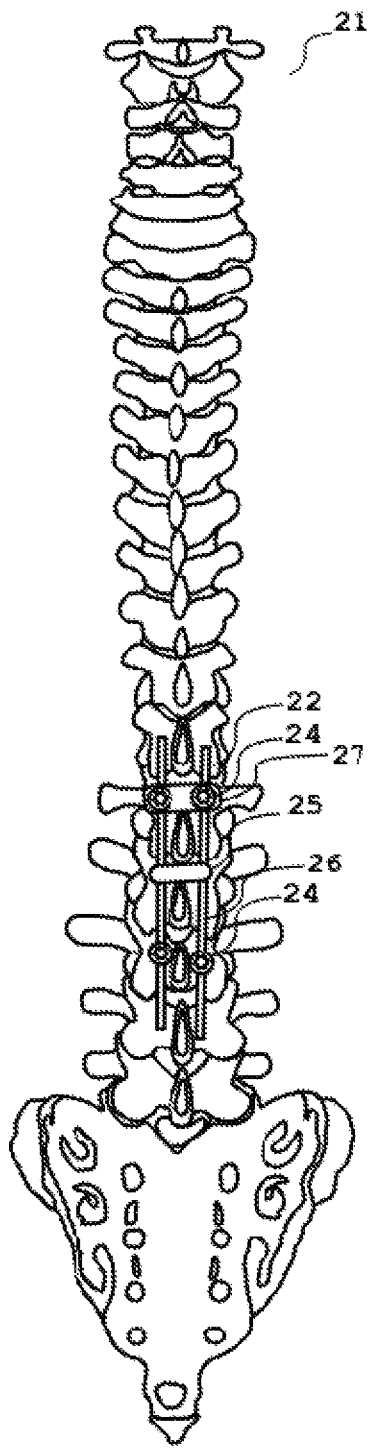
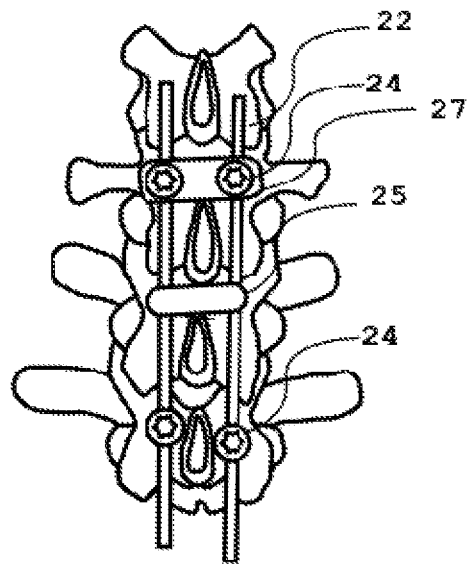
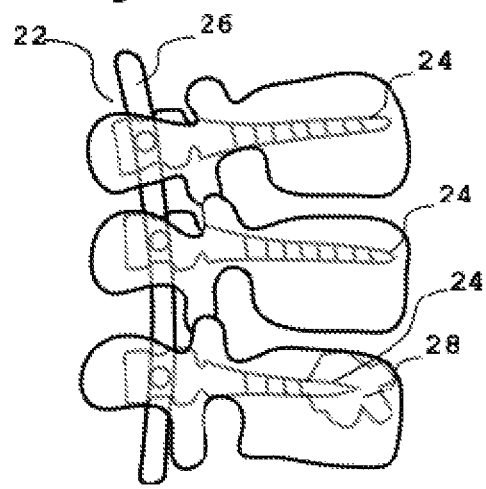
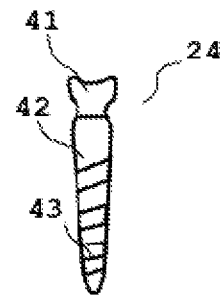

METHOD AND DEVICE FOR MEDICAL IMAGING FOR REPRESENTING A 3D VOLUME CONTAINING AT LEAST ONE INTRODUCED FOREIGN OBJECT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to medical imaging for representing a 3D volume containing at least one introduced foreign object.

Description of the Related Art

In medicine, there are a number of imaging methods which contain information about the structure of foreign objects. Some of the most commonly used imaging methods are based on X-ray imaging; alternative imaging methods can be based on ultrasound and the magnetic properties of foreign objects or regions to be examined.

Current methods can, on the basis of a plurality of images, generate three-dimensional representations/images.

Possible fields of application of medical imaging methods are orthopaedics, traumatology and neurosurgery with a focus on monitoring the position of foreign objects in an object to be examined/patient.

In order to monitor the position of at least one foreign object, individual foreign object, or individual foreign object component introduced into an object to be examined or into a patient by a physician, a set of measurement data (e.g., a plurality of 2D projections) is recorded, a 3D volume is reconstructed therefrom, and the 3D volume is displayed on a screen. The resulting and represented 3D volume allows the users to assess the position of the foreign object in different layer orientations, also called multiplanar reformation (MPR). Usually, neither the imaging device nor the display program for the MPR is provided with information about the existence of one or more foreign objects. Rather, said foreign objects are represented like all other contents of the MPR, in particular the patient anatomy.

Methods which resolve in three dimensions generate volume data which include a spatial distribution of the corresponding physical quantity and which are assigned to the spatial points contained in the corresponding volume. A point of such a three-dimensional arrangement is called a voxel and is usually represented as a gray scale value. When a voxel is displayed, it is imaged on a pixel of a two-dimensional pixel array of a display device, for example a screen. This is referred to as volume rendering, in particular when the volume is represented in a perspective view. In contrast to MPR, the representation here is preferably partially transparent, so that the volume as a whole can be seen and those structures which are located in the background in the respective perspective are not completely covered by structures located in front of them.

The user is thus not offered any assistance in identifying and referring to the introduced foreign objects or individual foreign objects, in particular in representing them in a characterizing manner.

Various possibilities of brightness and contrast scale adjustment, so-called windowing, exist for displaying the recorded area on a display device. A possible representation of windowing is so-called automatic windowing. In this case, a scale is created on the basis of the minimum and maximum gray scale values of the recorded area. Automatic windowing can select a scale that is not optimal for the user.

An alternative brightness and contrast scale setting is the manual setting of the scale by the user, which is time-consuming and constantly requires user input and editing.

The document DE 102014205820A1 discloses a method which automatically and semi-automatically provides for the selection of a layer which contains the axis of an individual foreign object and which optimally represents the position and orientation of this individual foreign object. In the three-dimensional case, the orientation of the sectional plane can be determined partially automatically and partially manually by the user. Segmentation and highlighted representation of the identified individual foreign objects is not disclosed.

A segmentation of an individual foreign object into individual foreign object components as well as an identification of the individual foreign object components by means of color marking is disclosed in "Model-Based Tomographic Reconstruction of Objects Containing Known Components", Stayman et al., pp. 1837-1848 IEEE (2012). Segmentation of the foreign objects into individual foreign objects is not disclosed.

SUMMARY

Embodiments of the present technology may improve the recognition, segmentation and representation of foreign objects in the representation of reconstructed volume data.

In some embodiments, a medical imaging method may be used to represent a reconstructed 3D volume containing at least one introduced foreign object comprising at least one individual foreign object composed of at least one individual foreign object component, based on the steps: provision of a 3D volume containing voxels of at least one foreign object and voxels of tissue surrounding the at least one foreign object, identification of the voxels of the at least one foreign object by application of a processing rule, segmentation of the voxels of the at least one foreign object from the voxels of the tissue surrounding the at least one foreign object while maintaining the 3D volume, generation of a synthetic volume from a residual volume and the volume of the at least one foreign object, representation of the synthetic volume on a display device using a windowing system.

BRIEF DESCRIPTION OF THE DRAWINGS

FIGS. 2a-2c are schematic representations of a spine with an introduced foreign object.

FIG. 3 is a schematic representation of a screw.

DETAILED DESCRIPTION

Figure 1:
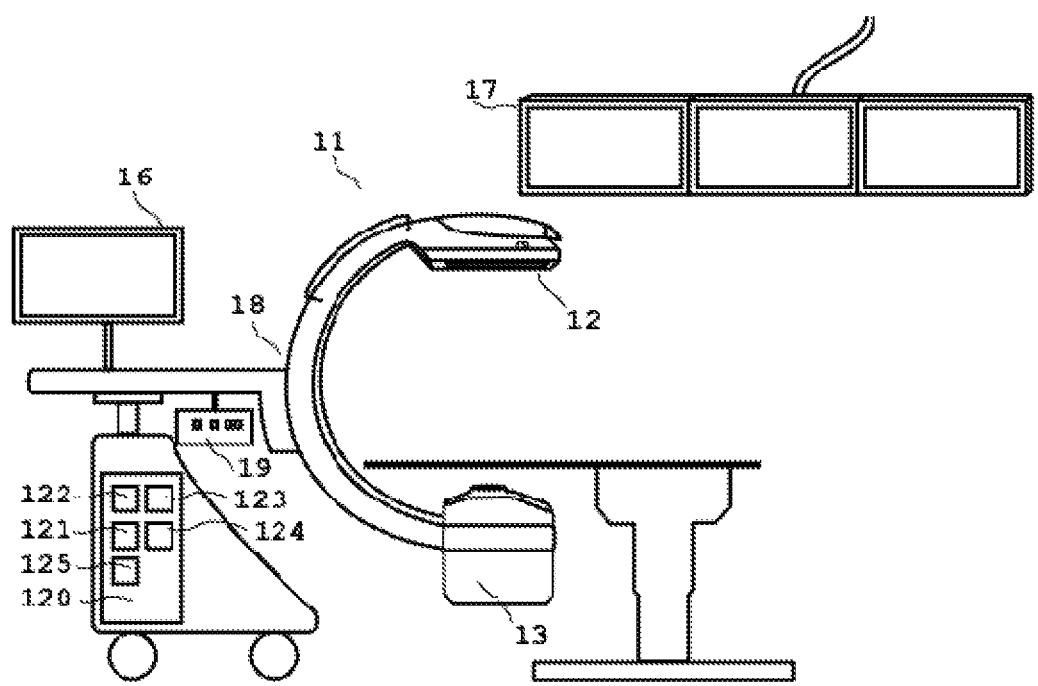
FIG. 1 illustrates a C-arm X-ray system with a device for displaying a 3D X-ray volume.

Systems and methods according to the present technology provide for identifying at least one foreign object which differs in its physical properties from the surrounding body tissue. Typical foreign objects can be, for example, metallic implant structures such as knee, hip, shoulder, vertebral implants or structures composed of individual foreign objects, where an individual foreign object can be, for example, a screw, hollow screw, nail, plate, Kirschner wire, connecting structure, in particular a connecting rod, a tool, or an X-ray positive marker. Such an individual foreign object includes at least one individual foreign object component. For example, the individual foreign object components of a screw can be the screw head, screw thread and the screw shank.

Foreign objects have invariable shapes and volumes. The method according to the present technology can also be used for volume/shape-changeable contrast medium volumes.

The methods according to the present technology may be based on the presence of a 3D volume. Said 3D volume is either recorded during an interventional procedure by means of a 3D scan or loaded from a patient archive. After reconstruction of the 3D volume, the voxels of the at least one foreign object, which is surrounded by voxels of the surrounding tissue, are identified. According to the present technology, foreign objects can be, for example, artificial joints, constructions of screws, plates and rods, combinations of artificial joints and constructions of screws, plates and rods. The voxels of the at least one foreign object are identified by applying a processing rule. In this case, the voxels of the 3D volume that are to be assigned to the at least one foreign object may be automatically determined. For example, in the case of X-ray computed tomography, metal objects can be identified via their comparatively high absorption of X-rays and, from this, a partial volume, which contains voxels with high X-ray absorption values or, in the case of computed tomography images, high Hounsfield units (HU), is determined. Said voxels in the partial volume can be automatically assigned, without user intervention, to one or more foreign objects in the anatomy. Then a synthetic volume including the residual volume and the partial volume of the segmented foreign object can be generated. Synthetic MPRs can be derived from the synthetic volume.

The result of the generation may be displayed on a display device.

One advantage of the methods according to the present technology is that the user is offered assistance in identifying the at least one foreign object introduced.

It is provided that one or more foreign objects are (automatically) recognized in an X-ray volume without user intervention and that the recognized foreign objects are displayed on a display in a 3D view of the X-ray volume. The foreign objects can be recognized on the basis of the atomic number, the material from which the at least one foreign object is made, the structure and geometry of the at least one foreign object.

It is provided to modify the 3D view in a known manner via a user interface (e.g., a Graphical User Interface, GUI) by means of a user intervention and to manually select and orient sectional planes, where it is possible for the sectional images of the selected sectional planes of the X-ray volume to be displayed on the display together with the 3D view, and where it is possible for the one or more foreign objects/individual foreign objects/individual foreign object components contained in the sectional images to be displayed in a highlighted manner. An advantage of a 3D view is that a plurality of or all foreign objects can be displayed by this type of display, while in an MPR sectional plane representation, depending on the setting of the sectional planes, usually only a limited number of foreign objects can be visible.

It is further provided to differently identify or highlight the one or more foreign objects, individual foreign objects, or individual foreign object components. The marking is preferably carried out through a different coloring, hatching or numbering. It is advantageous in this embodiment that the navigation between the foreign objects, individual foreign objects, or individual foreign object components and the exchange of information about such objects with other persons can be made easier and thus accelerated for the user.

Another aspect provides that the voxels of the boundaries of the one foreign object or of the plurality of foreign objects, individual foreign objects, or individual foreign object components can be marked.

Furthermore, provision is made for the positions and/or orientations of the one or more foreign objects, individual foreign objects, or individual foreign object components to be represented with respect to one another, so that the user/physician is provided with an overview so as to be able to assess the positions and/or orientations of the one foreign object, individual foreign object, or individual foreign object component or of the plurality of foreign objects, individual foreign objects, or individual foreign object components.

Provision is made for a user to be able to modify, rotate, move, and enlarge/reduce the representation of the 3D view in such a way that he obtains a desired view of a selected foreign object and can select sectional planes in the 3D representation with respect to the represented foreign object.

For the display, the user can choose, among other things, between an HU value-based strategy or a data-based strategy. When using the data-based strategy, an adapted windowing function f(P1, P2, . . . , Pn) can be calculated from at least one or more percentiles P1 . . . Pn from all the images. This function can additionally be adapted by the user.

When calculating the windowing, in particular the percentiles, a special treatment of the sections in which one or more foreign objects are located can preferably take place. Thus, the windowing can be adapted specifically to the representation of organs, or the anatomy, preferably to the individual foreign object components that are of interest for a specific application. For example, in the representation of screws introduced into vertebral bodies, the windowing for the representation of these screws can be adapted in a manner which ignores the often more strongly absorbing and uninteresting connecting elements, for example connecting rods, between these screws.

It is further provided to determine different windowing settings for layer representations and volume rendering.

Based on the segmentation, it is further provided that a subset of the voxels of the foreign objects, or a subset of the voxels of the individual foreign objects, or a subset of the voxels of the individual foreign object components, can be taken into account in the calculation of the windowing, so that windowing values are calculated which are particularly suitable for viewing/displaying bone structures, soft parts, and/or one or more foreign objects, individual foreign objects, or individual foreign object components.

Furthermore, there is an option to transparently display one or more foreign objects, individual foreign objects, or individual foreign object components. Transparency can vary from 0% (solid display) to 100% (fade-out). Said transparent representation can also refer in particular to the coloring of the foreign objects, individual foreign objects, or individual foreign object components. In order to better orient the user in the 3D volume, provision is also made for said transparent representation in the volume representation to be adapted to the current layer representation. Thus, for example, when the user changes a displayed layer, the distance of all foreign objects/individual foreign objects/ individual foreign object components from the currently changed layer can be calculated in real time and the transparency of the color representation in the volume representation can be selected to be all the greater, the further away these objects are from the selected layer. As a result, for example, a screw, which is just visible in a layer representation, is represented with a higher color intensity in the volume than that which is not contained in the selected layer representation. Furthermore, provision is made for such a distance-dependent representation to be realized by means of features other than a color or its transparency, for example by means of an object marking in the 3D volume, which is visible only when an object is located within or near at least one of the illustrated layers.

According to the present technology, the steps of the method may be implemented by software; in particular, the delimitation between the voxel of the foreign object and the voxel of the tissue is preferably carried out by means of a contrast method.

Depending on the identified at least one separate foreign object, segmentation into its individual foreign objects and segmentation of the individual foreign objects into its individual foreign object components can preferably also take place.

The voxels of a foreign object can be segmented into voxels of its individual foreign objects and its individual foreign object components based on the geometric shape of the foreign object to be identified.

In one aspect, the segmentation of the voxels of a foreign object into voxels of its individual foreign objects and its individual foreign object components takes place by a voxel-by-voxel calculation of a zero-, one- or multi-dimensional structure tensor with subsequent determination and evaluation of its eigenvalues and eigenvectors.

Alternatively, foreign objects from a database can be used for the segmentation, for example by means of a complete and/or partial template matching of the voxels that are connected as a foreign object, in order to determine the voxels of the individual foreign objects and the voxels of the individual foreign object components of the foreign object.

It is further provided that the method can be implemented through learning algorithms. In this case, the method can access previous identifications and segmentations which have been stored in a memory and thus accelerate the identification of new foreign objects and individual foreign objects and/or individual foreign object components.

An embodiment is expedient in which the at least one foreign object in the representation of the synthetic volume on the display device is supplemented by an adapted model of the foreign object, individual foreign object and individual foreign object component or is overlain by the representation of an adapted model of the at least one foreign object. Said model can be loaded from a database. Replacement of the at least one identified foreign object is advantageous if the foreign object is afflicted by artifacts or is displayed noisy.

The present technology further provides a device for recording a 3D volume with at least one introduced foreign object. Said foreign object includes at least one individual foreign object which is composed of at least one individual foreign object component. The device contains an X-ray apparatus by means of which a 3D volume data set which contains at least one foreign object can be generated. It also comprises a computer with a memory, a reconstruction unit, and an image processing unit. The reconstruction unit can reconstruct the 3D volume from the received set of measurement data. Furthermore, the completely reconstructed X-ray volume can solely be received. In that case, the reconstruction unit may be implemented outside of the computer, but in the overall system. An image processing unit generates a 3D view of the 3D volume with variable 3D views and/or definition of sectional planes for sectional image representations. Furthermore, the device may contain a GUI with an image output unit and an input unit with which the image processing unit and the control unit can change the sectional planes.

A largely software-based implementation of the methods of the present technology has the advantage that even previously used methods for foreign object recognition image recording systems can be retrofitted in a simple manner by a software update in order to operate according to the invention. In this respect, the objects of the present technology are also achieved by a corresponding computer program product having a computer program which can be loaded directly into a memory device of an image recording system, for example a conical beam computer tomograph, having program sections in order to execute the steps of the methods according to the present technology when the computer program is executed in the control device. In addition to the computer program, such a computer program product may optionally comprise additional components such as documentation and/or additional components, including hardware components for using the software.

A computer-readable medium, for example a memory stick, a hard disk or another portable or permanently installed data carrier, on which the program sections of the computer program which can be read in and executed by a computer unit of the control device are stored, can be used for transport to the control device and/or for storage on or in the control device. A connection to a hospital information system connected to a network, to a radiology information system or to a global network, in which systems are stored the program sections of the computer program which can be read in and executed by a computer unit of the control device, can also be used for the transport. The computer unit can have, for example, one or more cooperating microprocessors or the like for this purpose.

Provision is made for the device to have a modality from the group including a C-arm and a computed tomograph. Other imaging devices and modalities are contemplated within the scope of the present technology.

A C-arm X-ray system 11, which is suitable for realizing the present methods for recording projection images of a scan, is shown schematically in FIG. 1.

The C-arm 18 carries an X-ray generator 13 at one end and an X-ray image detector 12 at the other end and opposite the X-ray generator 13. The C-arm 18 can be adjusted in a motor-controlled manner in a plurality of axes in space, the axes having sensors for detecting the extent of the adjustment.

The apparatus further includes a computer 120 having a memory unit 121, a reconstruction unit 122, a control unit 123, an image processing unit 124, and a network interface 125.

The projections used for reconstructing the 3D volume can be stored or loaded into the memory unit 121. Said projections can either be loaded from a server or recorded by means of the C-arm X-ray system 11 before or during an intervention. The reconstruction unit 122 reconstructs the 3D volume from the projections present in the memory unit 121. An image processing unit 124 creates a 3D view of the 3D volume with variable 3D views and for defining sectional planes for sectional image representations. Furthermore, the device includes a GUI with an image output unit 16 and an input unit 19, with which the image processing unit 124 and the control unit 123 can change the sectional planes.

By means of the network interface 125, the reconstructed 3D volume and sectional planes can additionally be displayed on other display devices 17.

An example method is explained with reference to FIGS. 2a, 2b and 2c. FIG. 2a shows a spine 21 with an introduced foreign object 22. Said foreign object 22 includes a plurality of individual foreign objects: four screws 24, two connecting rods 26, a connecting piece 25, and two connecting pieces with screw holes 27. In FIG. 2b, the foreign object 22 is shown in an enlarged view.

FIG. 2c shows another foreign object 22 in a lateral cross-sectional view. It can be seen in this view that three screws 24 have been inserted into a spine 21, of which one screw 24 has been secured with cement 28. The methods according to the present technology likewise make it possible to identify the voxels of the cement 28 which was introduced as an individual foreign object.

FIG. 3 shows a screw 24 which is recognized by the method according to the present technology as an individual foreign object. Such a screw 24 can include a plurality of individual foreign object components. The screw 24 illustrated in FIG. 3 includes a screw head 41, a screw shank 42 and a screw thread 43. Said individual foreign object components can be recognized by the method according to the invention on the basis of their shape, among other things, and separately identified and/or displayed transparently.

Figure 4:
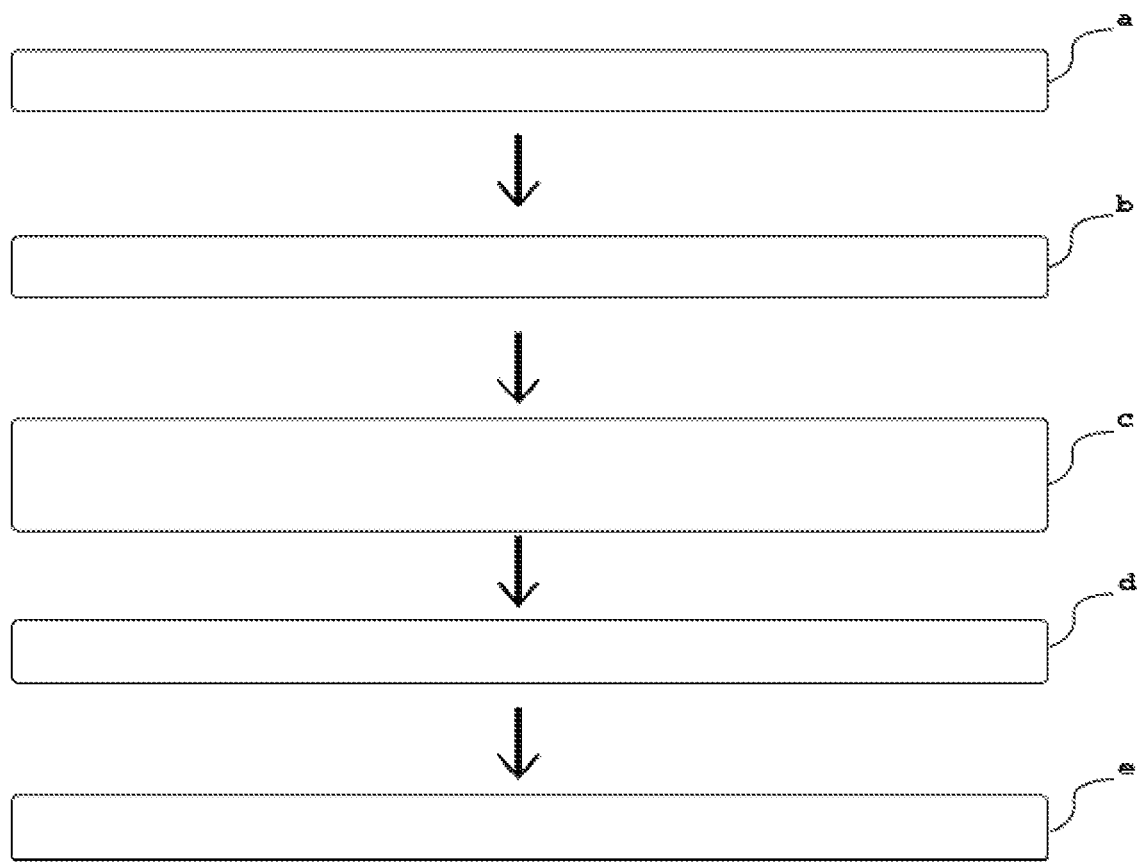
FIG. 4 is a schematic representation of process steps of an example method in accordance with the present technology.

In FIG. 4, the essential steps of the method are illustrated by means of an exemplary embodiment.

At the beginning of the method, in step a, a 3D data set with at least one foreign object can be received, for example it can be loaded from an external memory into the internal memory unit. The 3D data set can also be recorded directly by the 3D X-ray apparatus.

In a further step b, the 3D data set can be examined voxel-by-voxel, wherein the voxels of the at least one foreign object and of the surrounding anatomical structures, for example bones and tissue, can be identified.

In the subsequent step c, the identified voxels are segmented, so that the voxels of the at least one foreign object are associated with the latter and the voxels of the anatomical structures, for example bones and tissue, can be associated with the environment.

In a further step d, a synthetic volume is generated from the segmented voxels, which is ultimately displayed on at least one display device (step e).

LIST OF REFERENCE NUMERALS AND SYMBOLS

11 C-arm X-ray system
12 X-ray image detector
13 X-ray generator
16 Image output unit
17 Display
18 C-arm
19 Input unit
120 Computer
121 Memory unit
122 Reconstruction unit
123 Control unit
124 Image processing unit
125 Network interface
21 Spine
22 Introduced foreign object
24 Screw
25 Connector
26 Connecting rods
27 Connectors with screw holes
28 Cement
41 Screw head
42 Screw Shank
43 Screw thread Other, particularly advantageous embodiments and further developments of the present technology shall become apparent from the dependent claims and the description, where in this case the independent claims of one category of claims can also be further developed analogously to the dependent claims of another category of claims; and, in particular, individual features of different exemplary embodiments or variants can be combined to form new exemplary embodiments or variants.

What is claimed is:

1. A method of medical imaging for representing a 3D volume with at least one foreign object introduced into a tissue, which foreign object comprises at least one individual foreign object, wherein each individual foreign object comprises at least one individual foreign object component, the method comprising:
   providing a 3D volume containing voxels of the at least one foreign object and voxels of tissue surrounding the at least one foreign object;
   identifying the voxels of the at least one foreign object by application of a processing rule;
   segmenting the voxels of the at least one foreign object from the voxels of the tissue surrounding the at least one foreign object while maintaining the 3D volume;
   segmenting, in a second segmentation step, the at least one foreign object into its individual foreign objects;
   segmenting, in a third segmentation step, the individual foreign objects of the at least one foreign object into the individual foreign object components of the individual foreign objects;
   generating a synthetic volume from a residual volume and the volume of the at least one foreign object; and
   representing the synthetic volume on a display device,
   wherein at least one of the second segmentation step and the third segmentation step comprises segmenting two or more contiguous groups of voxels based on calculation of a structure tensor.

2. The method of claim 1, wherein the segmentation of the voxels of the at least one foreign object, the second segmentation of the volumes of the at least one individual foreign object and the third segmentation of the volumes of the individual foreign objects into the individual foreign object components take place by means of contrast methods.

3. The method of claim 1, wherein the segmentation of the at least one foreign object into individual foreign objects and the segmentation of the individual foreign objects into the individual foreign object components take place using information about their geometric shape.

4. The method of claim 1, wherein the voxels of the at least one individual foreign object are assigned to a tool, a screw, a hollow screw, a nail, a plate, a connecting structure or an X-ray positive marker.

5. The method of claim 1, wherein the at least one foreign object in the representation of the synthetic volume on the display device is supplemented by an adapted model of the at least one foreign object, individual foreign object and individual foreign object component, or is overlain by the representation of an adapted model of the at least one foreign object.

6. The method of claim 1, wherein the method is carried out by learning algorithms.

7. The method of claim 1, wherein the representations of the individual foreign objects and of the individual foreign object components are identified.

8. The method of claim 7, wherein the representations of the individual foreign objects and individual foreign object components are identified by coloring.

9. The method of claim 7, wherein the representations of the boundaries of the foreign objects, of the individual foreign objects and individual foreign object components are identified.

10. The method of claim 1, wherein one or more vectors representing the orientations of the foreign objects, of the individual foreign objects or of the individual foreign object components with respect to one another are represented on the display device.

11. The method of claim 1, wherein the synthetic volume is represented on the display device using a windowing function which determines a brightness scale or a contrast scale of the represented synthetic volume based on a subset of the foreign objects or a subset of the individual foreign objects or a subset of the individual foreign object components and ignoring at least one of the foreign objects, the individual foreign objects, or the individual foreign object components.

12. The method of claim 11, wherein the brightness scale or the contrast scale calculated based on the subset is applied to the entire represented synthetic volume.

13. A device for carrying out the method according to claim 1, the device comprising:

a device for receiving a 3D volume containing the at least one foreign object;

a computer with a memory unit;

an image processing unit for generating a 3D view of the 3D X-ray volume with variable 3D views and for defining sectional planes for sectional image representations; and a graphical user interface with an image output unit and an input unit for the image processing unit and a control unit for changing the sectional planes.

14. The device of claim 13, wherein the received 3D volume is the result of a reconstruction from measurement data of a modality from a group of modalities, the group containing at least one C-arm X-ray apparatus and a computer tomograph.

15. A tangible, non-transitory, computer-readable storage medium having stored thereon a computer program which can be loaded directly into a memory unit of a control unit of a conical beam computer tomograph, in particular a C-arm X-ray device, with program sections that cause the conical beam computer tomograph to perform the method according to claim 1 when the computer program is executed in the control unit of the conical beam computer tomograph.

16. A tangible, non-transitory, computer-readable storage medium having stored thereon program sections which can be read in and executed by a computer unit in order to perform the method according to claim 1 when the program sections are executed by the computer unit.

* * * * *